US008709741B2

(12) United States Patent
Deregnaucourt et al.

(10) Patent No.: US 8,709,741 B2
(45) Date of Patent: Apr. 29, 2014

(54) METHODS OF DIAGNOSING A PLASMODIUM INFECTION

(75) Inventors: Christiane Deregnaucourt, Châtenay-Malabry (FR); Gérard Lambeau, Grasse (FR); Carole Guillaume, Nanterre (FR); Joseph Schrevel, Civaux (FR)

(73) Assignees: Centre National de la Recherche Scientifique, Paris (FR); Universite de Nice Sophia Antipolis, Nice Cedex (FR); Museum National d'Histoire Naturelle, Paris (FR)

( * ) Notice: Subject to any disclaimer, the term of this patent is extended or adjusted under 35 U.S.C. 154(b) by 0 days.

(21) Appl. No.: 13/513,465

(22) PCT Filed: Dec. 3, 2010

(86) PCT No.: PCT/IB2010/055580
§ 371 (c)(1), (2), (4) Date: Jul. 24, 2012

(87) PCT Pub. No.: WO2011/067740
PCT Pub. Date: Jun. 9, 2011

(65) Prior Publication Data
US 2012/0282238 A1 Nov. 8, 2012

(30) Foreign Application Priority Data
Dec. 3, 2009 (EP) .................................... 09290901

(51) Int. Cl.
*C12Q 1/44* (2006.01)

(52) U.S. Cl.
USPC .......................................................... 435/19

(58) Field of Classification Search
USPC .......................................................... 435/19
See application file for complete search history.

(56) References Cited

U.S. PATENT DOCUMENTS 6,043,231 A * 3/2000 Pruzanski et al. ............ 514/152
2008/0031951 A1 * 2/2008 Guichard et al. ............. 424/474

OTHER PUBLICATIONS

International Search Report and Written Opinion for Application No. PCT/IB2010/055580 dated Mar. 9, 2011.
Guillaume, C. et al., *Anti-Malarial Properties of the Full Set of Human Secreted Prospholipases A2; Potent Effects of Group IIF and X Enzymes*, Article 4, Resultats, Dec. 4, 2009, p. 88.
Guillaume, C. et al., *Anti-Plasmodium Properties of Group IA, IB, IIA and III Secreted Phospholipases $A_2$ Are Serum-Dependent*, Toxicon 43 (2004) 311-318.
Kudo, I. et al., *Phospholipase $A_2$ Enzymes*, Prostaglandins & Other Liquid Mediators 68-69 (2002) 3-58.
Lucas, K. K. et al., *Distinguishing Phospholipase $A_2$ Types in Biological Samples by Employing Group-Specific Assays in the Presence of Inhibitors*, Prostaglandins & Other Lipid Mediators 77 (2005) 235-248.
Moll, G. N. et al., *Selective Elimination of Marlaria Infected Erthyrocytes by a Modified Phospholipase $A_2$* in Vitro, Biochimica et Biophysica Acta, 1024 (1990) 189-192.
Murakami, M. et al., *Emerging Roles of Secreted Phospholipase $A_2$ Enzymes; Lessons From Transgenic and Knockout Mice*, Biochimie 92 (2010) 561-582.
Nevalainen, T. J. et al., *Time-Resolved Fluoroimmunoassays of the Complete Set of Secreted Phospholipases $A_2$ in Human Serum*, Biochimica et Biophysica Acta 1733 (2005) 210-223.
Schaloske, R. H. et al., *The Phospholipase $A_2$ Superfamily and Its Group Numbering System*, Biochemica et Biophysica Acta 1761 (2006) 1246-1259.
Vadas, P. et al., *Increased Serum Phospholipase $A_2$ Activity in Malawian Children With Falciparum Malaria*, Am. J. Trop. Med. Hyg. 49(4) (1993) 455-459.
Vadas, P. et al., *Induction of Circulating Group II Phospholipase A2 Expression in Adults with Malaria*, Infection and Immunity, vol. 60, No. 9 (Sep. 1992) 3928-3931.
Ait-Oufella, H. et al., 2010. Circulation Abstract 5459, ATVB meeting 2009.
Boilard E. et al., 2010. EMBO Mol. Med. 2: 172-187.
Bostrom, M. A. et al., 2007 Arterioscler. Thromb. Vase. Biol. 27: 600-606.
Chen, J. et al., 1994. J. Biol. Chem. 269: 2365-2368.
Cupillard, L. et al., 1997. J. Biol. Chem. 272: 15745-15752.
Deregnaucourt, C. et al., 2000. J. Biol. Chem. 275: 39973-39980.
Eckey, R. et al., 1997. Atherosclerosis 132: 165-176.
Franson, R. et al., 1974. J. Lipid Res. 15: 380-388.
Gelb, M. H. et al., 2000, J. Biol. Chem. 275: 39823-39826.
Gesquiere, L. et al., 2002. Biochemistry 41: 4911-4920.
Gilroy, D. W. et al., 2004. Faseb J. 18: 489-498.
Gora, S. et al., 2006. Biochim. Biophys. Acta 1761: 1093-1099.
Grellier, P. et al., 1990, C. R. Acad. Sci. III. 311: 361-367.
Guillaume, C. et al., 2006. J. Lipid Res. 47: 1493-1506.
Havel, R. J. et al., 1955. J. Clin. Invest. 34: 1345-1353.
Ishimoto Y . et al., 2003. BBA. 1642: 129-138.
Ishizaki, J. et al., 1999. J. Biol. Chem. 274: 24973-24979.
Jonsson-Rylander, A. C. et al., 2008. Curr. Atheroscler. Rep. 10: 252-259.
Koduri, R. S. et al., 2002. J. Biol. Chem. 277: 5849-5857.
Kramer, R. M. et al., 1989. J. Biol. Chem. 264: 5768-5775.
Lambeau, G. et al., 2008. Annu. Rev. Biochem. 77: 495-520.
Maguire, P.A. et al., 1991. Parasitology. 102: 179-186.
Menschikowski et al., 2006.
Nakanishi, M. et al., 2006. Biochim. Biophys. Acta 1761: 1335-1343.
Nevalainen, T. J. et al., 2008. Biochim. Biophys. Acta 1781: 1-9.
Oduola, A. M. et al., 1998. Am. J. Trop. Med. Hyg. 58: 625-629.
Prusanski, W. et al., 1998. J. Lipid Res. 39: 2150-2160.
Pruzanski, W. et al., 2005. Biochim. Biophys. Acta. 1736: 38-50.
Rosengren, B. et al., 2006. Biochim, Biophys. Acta 1761: 1301-1308.

(Continued)

Primary Examiner — Ralph Gitomer
(74) Attorney, Agent, or Firm — Alston & Bird LLP

(57) ABSTRACT

The present disclosure provides in vitro methods of diagnosing a *Plasmodium* infection in a subject. The methods include measuring the serum concentration of at least one secreted phospholipase $A_2$ selected from the group consisting of GIIF, GV and GX sPLA$_2$s, in a blood sample from the subject. The disclosure also relates to a kit for carrying out the disclosed methods and pharmaceutical compositions comprising a recombinant mammalian GIIF, GV or GX sPLA$_2$, or a combination thereof.

13 Claims, 5 Drawing Sheets

(56) References Cited

OTHER PUBLICATIONS

Rouault, M. et al., 2003. Biochemistry 42: 11494-11503.
Rouault, M. et al., 2007. Biochemistry 46: 1647-1662.
Sato H. et al., 2008. J. Biol. Chem. 283: 33483-33497.
Seilhamer, J. J. et al., 1986. DNA 5: 519-527.
Seilhamer, J. J. et al., 1989. J. Biol. Chem. 264: 5335-5338.
Sibmooh, N. et al., 2004. Lipids Health Dis. 3:15.
Singer, A. G. et al., 2002. J. Biol. Chem. 277: 48535-48549.
Six, D. A. et al., 2000. Biochim. Biophys. Acta 1488: 1-19.
Smart, B. P. et al., 2006. J. Med. Chem. 49: 2858-2860.
Sun, G. Y. et al., 2007. J. Neurochem. 103: 1-16.
Suzuki, N. et al., 2000. J. Biol. Chem. 275: 5786-5793.
Talvinen, K. A. et al., 2002. Comp. Biochem. Physiol. B. Biochem. Mol. Biol. 132: 571-578.
Trager, W. et al., 1976. Science. 193: 673-677.
Triggiani, M. et al., 2005. J. Allergy Clin. Immunol. 116: 1000-1006.
Valentin E. et al., 1999. J. Biol. Chem. 274: 31195-31202.
Valentin E. et al., 2000a. J. Biol. Chem. 275: 7492-7496.
Valentin E. et al., 2000b. Biochem. Bioph. Res. Co. 279: 223-228.
Valentin E. et al., 2000c. Biochim. Biophys. Acta. 1488: 59-70.
Van der Heyde, H.C. et al., 2006, TRENDS in Parasitol. 22: 503-508.
Venable, M.E. et al., 1993. J. Lipid Res. 34: 691-702.
Verheij, H. M. et al., 1981. Rev. Physiol. Biochem. Paramacol. 91: 91-203.
Von Allmen, C. E. et al., 2009. Proc. Natl. Acad. Sci. USA. 106: 11673-11678.
Warhurst D. C. et al., 1996. J. Clin Pathol. 49: 533-538.
Webb, N. R. et al., 2003. Arterioscler. Thromb. Vasc. Biol. 23: 263-268.
Wijewickrama et al., 2006.
WHO, Management of Severe Malaria, 2000. A Practical Handbook, $2^{nd}$ ed. Geneva,: World Health Organization.

\* cited by examiner

METHODS OF DIAGNOSING A PLASMODIUM INFECTION

This application is a national stage application filed under 35 U.S.C. 371 of International Application No. PCT/IB2010/055580, filed Dec. 3, 2010, which claims priority to European Application No. 09290901.9, filed Dec. 3, 2009.

FIELD

The present invention relates to the use of secreted phospholipases $A_2$ in the diagnosis and treatment of malaria.

BACKGROUND

Human tissues secrete low molecular weight phospholipases $A_2$ (named "secreted $PLA_2$s" or "$sPLA_2$s"; EC 3.1.1.4) which catalyse the hydrolysis of phospholipids at the sn-2 position to release fatty acids (such as arachidonic acid) and lysophospholipids. Lysophospholipids and fatty acids are biologically active as precursors of potent bioactive lipid mediators. Such lipid mediators are important players in inflammation, cancer and neurodegenerative diseases (Kudo and Murakami 2002; Nakanishi and Rosenberg, 2006; Sun et al., 2007). Besides the possible role of human $sPLA_2$s in lipid mediator production, accumulated evidence indicate that these enzymes are likely to participate in innate immunity, especially in the first line of host defence against bacteria and other pathogens (Lambeau and Gelb, 2008; Nevalainen et al., 2008). Human $sPLA_2$s share common characteristic features: numerous disulfide bonds, low molecular masses (13-18 kDa), catalytic histidinyl and aspartyl residues, and millimolar concentrations of calcium requirement for optimal catalytic activity. However, the different human $sPLA_2$ paralogs are not closely related isoforms since the amino acid identity between any two of them is comprised between 15% to 50% Furthermore, the different paralogs have very distinct enzymatic properties (Singer et al., 2002) as well as distinct tissue distribution, regulation of expression and emerging biological functions (Murakami et al., 2010).

The family of human $sPLA_2$s comprises so far nine catalytically active enzymes and two catalytically inactive sPLA2-like proteins (XIIB and otoconin-95). They have been classified as groups (G) IB (Seilhamer et al., 1986), IIA (Kramer et al., 1989; Seilhamer et al., 1989), IID (Ishizaki et al., 1999), IIE (Suzuki et al., 2000), IIF (Valentin, 2000b), III (Valentin, 2000a), V (Chen et al., 1994), X (Cupillard et al., 1997) and XIIA (Gelb et al; 2000), XIIB (Rouault, M., et al. 2003) and otoconin-95 (see also for reviews Schaloske and Dennis, 2006; Lambeau and Gelb, 2008 and Murakami et al., 2010). The GIB $sPLA_2$ (pancreatic type $sPLA_2$) and GIIA $sPLA_2$ (inflammatory type $sPLA_2$) were the two first human $sPLA_2$s identified in the 80's (Verheij et al., 1981 and Kramer et al; 1989). The other members of the human $sPLA_2$ family were cloned in the late 90's and after (see for review Valentin et al., 2000c and Murakami et al., 2010).

Different enzymatic properties and unique tissue distribution and/or cellular localizations of these $sPLA_2$s suggest distinct physiological role(s) for each enzyme (see for reviews Lambeau and Gelb, 2008 and Murakami et al., 2010). Some appear to play a role in several inflammatory diseases, such as groups IIA and V (Gilroy et al., 2004; Triggiani et al., 2005) and some exhibit bactericidal properties against Gram-positive and/or Gram-negative bacteria, such as groups IIA, X, V, XII, IIE, IB, IIF (Koduri et al., 2002; Lambeau and Gelb, 2008).

In fact, the different human $sPLA_2$s exert highly specialized and non redundant functions in different tissues and biological contexts (Murakami et al., 2010). Indeed:

- the different $sPLA_2$s are expressed in a limited number of tissues and cells, they can be found at different locations in a single tissue, and their expression is differentially regulated according to the disease stages (Murakami et al., 2010); e.g., detection of high levels of GIIA $sPLA_2$ at various inflamed sites suggests its involvement in pathogenesis of the inflammatory responses; its concentration in serum and tissues correlates with disease severity in several immune-mediated inflammatory pathologies (Kudo and Murakami, 2002; Nevalainen et al., 2008; Menschikowski et al., 2006);
- some $sPLA_2$s have high and specific enzymatic activities toward certain phospholipids while other $sPLA_2$s have very low activities towards many if not all types of phospholipids (Singer et al., 2002);
- some few $sPLA_2$s have the capacity to hydrolyze lipoproteins and produce lipid mediator release from cellular membranes (Singer et al., 2002 and Sato et al., 2008);
- some $sPLA_2$s, whatever they are highly or poorly enzymatically active, can bind to different soluble and membrane-bound proteins (Lambeau et al., 2008);
- there is emerging evidence indicating that some $sPLA_2$s exert different and even opposite roles within the same tissue in vivo; e.g., both GIIA and GV $sPLA_2$s are proatherogenic (Bostrom et al., 2007; Webb et al., 2003; Rosengren et al., 2006 and Jonsson-Rylander et al., 2008), while GX $sPLA_2$ appears to be anti-atherogenic (Ait-Oufella et al., 2009); in addition, GIIA $sPLA_2$ is proinflammatory while GV is anti-inflammatory in a mouse model of rheumatoid arthritis (Boilard et al., 2010);
- contrary to GIIA $sPLA_2$, GIID $sPLA_2$ appears to be anti-inflammatory in murine models of colitis and multiple sclerosis (von Allmen et al., 2009).

It appears from the foregoing that human $sPLA_2$s are currently considered as functionally distinct isoforms with different and sometime opposite biological roles.

In malaria-infected humans, abnormally elevated levels of circulating phospholipase $A_2$ activity have been observed in severe cases (Vadas et al., 1992 and 1993). In fact, the phospholipase A2 activity observed by Vadas et al. is attributed to the human GIIA $sPLA_2$, since the murine monoclonal antibodies 9C1 and 4A1 used by Vadas et al. (1992) are specific for the GIIA $sPLA_2$, and the synovial type group II $PLA_2$ detected by Vadas et al. (1993) is known as being the human GIIA $sPLA_2$ (see Nevalainen et al., 2005). Vadas and his colleagues have also disclosed that a recombinant human $PLA_2$ (in fact GIIA $sPLA_2$) selectively lyses human erythrocytes parasititized with *P. falciparum* and suggested that high level of endogenous circulating $PLA_2$ (i.e., GIIA $sPLA_2$) may contribute to hemolysis of parasitized erythrocytes in patients with malaria (Vadas et al., 1992), but they have not provided any data supporting these statements.

Five hundred million clinical cases of malaria are reported each year and mortality estimates range between 0.7 and 2.7 million. The vast majority of cases presents a non-specific febrile illness that is relatively easily terminated, but a minority of cases progresses to severe, life-threatening disease (WHO, Management of Severe Malaria, 2000. A practical handbook, $2^{nd}$ ed. Geneva: World Health Organisation). It is now currently accepted that severe malaria is an extremely complex multi-process and multi-system disorder. In human, the disease is caused by protozoan parasites of the genus *Plasmodium: P. falciparum, P. malariae, P. ovale* and *P.*

*vivax.* The life cycle of these human malaria parasites is essentially the same: first, sporozoites enter the bloodstream, and migrate to the liver. Then, they enter the liver cells (hepatocytes), where they multiply into merozoites, rupture the liver cells, and escape back into the bloodstream. Then, the merozoites enter red blood cells (erythrocytes), where they develop into ring forms, then trophozoites (a feeding form), then schizonts (a reproduction form), and then back into merozoites.

*P. falciparum* is the major cause of mortality, mostly through two main complications: cerebral malaria and severe anaemia. A central feature of *P. falciparum* infection is sequestration of mature forms (schizonts) of parasitized erythrocytes within the microvasculature of the major organs of the body, predominantly in brain, heart, lungs and small intestine. The events resulting in the development of cerebral malaria are multi-factorial, encompassing dynamic interactions between at least three processes: sequestration of parasitized erythrocytes in the brain, haemostasis and inflammation (Van der Heyde, 2006).

Diagnosis of malaria involves identification of the malaria parasite or its antigens in the blood of the patient. It can be performed by microscopy methods (e.g., by peripheral smear examination or Quantitative Buffy Coat (QBC) test), by immunoassays for malaria antigens (e.g., using rapid diagnostic tests (RDTs)) or by Polymerase Chain Reaction assays. However, the efficacy of the diagnosis depends on many factors, such as the different forms of the four *Plasmodium* species, the different stages of erythrocytic schizogony (asexual multiplication in the erythrocytes), the quantitative content of parasites in the blood (parasitemia), the persisting viable or non-viable parasites in the blood and the sequestration of the parasites in the tissues.

To date, there is no rapid and accurate method to assess the risk of developing severe and/or cerebral malaria due to *P. falciparum*. Only certain clinical symptoms such as hypoglycaemia, severe anaemia or high parasitemia, particularly when they are combined in a patient, can alert on possible complication, sometimes too late.

Many different antimalarial drugs are available to prevent and/or treat malaria, including schizonticides on erythrocytic forms of *Plasmodium*, such as amino-4-quinolines (e.g., chloroquine), amino-alcohols (e.g., quinine), sesquiterpens (e.g., artemisinin) and antimetabolites, schizonticides on the intra-hepatic forms of *Plasmodium* and gametocytocides, such as amino-8-quinolines (e.g., primaquine), endo-erythrocytic schizonticides active on endoerythrocytic trophozoites, such as quinine (which remains the standard anti-malarial drug in the management of severe forms of malaria), and combination thereof. However, parasite resistance to some antimalarial drugs is an increasingly serious problem.

Consequently, it appears from the foregoing that there is a need of developing new method of diagnosis of malaria, particularly *P. falciparum* malaria, and new treatments.

SUMMARY

The inventors have previously shown that group IA, IIA and III sPLA$_2$s from snake and insect venoms exhibit marked anti-*Plasmodium* properties in vitro (Deregnaucourt and Schrével, 2000; Guillaume et al., 2004). They have observed that venom sPLA$_2$s can exert indirect killing of *P. falciparum* by hydrolysis of serum lipoproteins contained in the parasite culture medium, generating toxic lipids, especially free fatty acids that mediate parasite death (Guillaume et al., 2006). Specifically, bee (*Apis mellifera*) venom sPLA$_2$ was demonstrated to act primarily via this indirect mechanism (Guillaume et al., 2006).

Now, the Inventors have investigated the anti-*Plasmodium* properties of human sPLA$_2$s. Surprisingly, they have shown in vitro that human GIIA sPLA$_2$ does not exhibit any inhibitory activity on standard *P. falciparum* cultures, suggesting that its role in malaria, if any, would not deal with direct elimination of the parasite, but that GIIF, GV and GX sPLA$_2$s are active against *P. falciparum*. In the case of GX sPLA$_2$, the most active sPLA$_2$ against *P. falciparum*, the parasiticidal effect results from enzymatic hydrolysis of both exogenous phospholipids from the culture medium and cellular phospholipids from infected erythrocytes. The Inventors have also shown that the anti-*Plasmodium* enzymatic activity of GX sPLA$_2$ is potentiated in the presence of the platelet-activating factor (PAF; a potent mediator of platelet aggregation and inflammation; Venable et al., 1993).

Further, the inventors have shown that i) the plasma level of hGIIA, hGIIF and hGV sPLA$_2$s is significantly increased in patients infected with *P. falciparum* and ii) a positive correlation between plasma levels of hGIIF and hGV sPLA$_2$s, and between plasma levels of hGIIA and hGIIF sPLA$_2$s is found in these patients (see Example 3 below). More specifically, significant increases of hGV and hGIIF sPLA$_2$s were found in patients with low parasitaemia, but not in patients with higher parasite levels. Further, it appears from the results obtained by the inventors that a specific combined increase of hGIIF and hGV sPLA$_2$s in plasma of patients with low parasitaemia may contribute to maintain parasitaemia under a deleterious threshold, and may be predictive of a favourable outcome in patients infected with *Plasmodium*.

The presence of other sPLA$_2$s besides hGIIA in serum from normal (healthy) subjects or septic shock patients (Nevalainen et al., 2005) has not been reported. Therefore, these results suggest that an increased plasma level of hGIIF and/or hGV sPLA$_2$s is specifically induced by the malaria parasite.

Based on these results showing a role of human GIIF, GV and GX sPLA$_2$s in *P. falciparum* infection and an increased plasma level of hGIIF and hGV sPLA$_2$s in *P. falciparum*-infected patients, diagnosing malarial infection can be carried out by specifically measuring the serum concentrations of GIIF, GV and/or GX sPLA$_2$: an increase in enzymatic activity (or plasma level) of at least one of these sPLA$_2$s in the serum of a subject indicating the presence of *Plasmodium* in said subject.

Accordingly, the present invention relates to an in vitro method of diagnosis of a *Plasmodium* infection, preferably a *P. falciparum* infection, in a subject, said method comprising the following steps:

a) measuring the serum concentration of at least one secreted phospholipase A$_2$ (sPLA$_2$) selected from the group consisting of GIIF, GV and GX sPLA$_2$, preferably GIIF and GX, or more preferably GIIF and GV sPLA$_2$s, in said subject, from a blood sample, b) comparing the serum concentration of GIIF, GV and/or GX sPLA$_2$s obtained in step a) with the reference serum concentration of GIIF, GV and/or GX sPLA$_2$s in subjects not infected with *Plasmodium* (healthy subjects) respectively, wherein a superior serum concentration of GIIF, GV and/or GX sPLA$_2$s in said blood sample from said subject compared to the reference serum concentration of GIIF, GV and/or GX sPLA$_2$s in subjects not infected with *Plasmodium*, is indicative that said subject is infected with *Plasmodium*.

A "subject" refers to a mammal, preferably a human. Advantageously, said subject has fever.

As used herein, "*Plasmodium*" refers to a parasite of the genus *Plasmodium*, preferably *P. falciparum, P. malariae, P. ovale* and *P. vivax*, and more preferably *P. falciparum*.

In a preferred embodiment of said method, in addition to the measurement of the serum concentration of GIIF, GV and/or GX sPLA$_2$s, the serum concentration of GIIA sPLA$_2$ is also measured, and compared to the reference serum concentration of GIIA sPLA$_2$ in subjects not infected with *Plasmodium*, wherein a superior serum concentration of GIIF, GV and/or GX sPLA$_2$s, and GIIA sPLA$_2$ in said blood sample from said subject compared to the reference serum concentration of GIIF, GV and/or GX sPLA$_2$s, and GIIA sPLA$_2$ in subjects not infected with *Plasmodium* is indicative that said subject is infected with *Plasmodium*.

The measurement of the serum concentration of the GIIA, GIIF, GV and GX sPLA$_2$s, can be carried out in vitro by measuring the catalytic activity of these four sPLA$_2$s respectively or by immunoassay. By way of example, the serum concentration can be determined by the ELISA as described in Vadas et al., 1992 and 1993 for GIIA sPLA$_2$ or by time-resolved fluoroimmonoassays (TR-FIA) as described in Nevalainen et al., 2005 for the GIIA, GIIF, GV and GX sPLA$_2$s.

In a preferred embodiment, the serum concentration of GIIF and GX, or GIIF and GV, or GV and GX is measured.

In another preferred embodiment, the serum concentration of GIIF, GV and GX is measured.

In another preferred embodiment, the serum concentration of GIIF and/or GV sPLA$_2$s, preferably GIIF and GV sPLA$_2$s, and optionally in addition GIIA sPLA$_2$, is measured. A superior serum concentration of GIIF and/or GV sPLA$_2$s, and optionally GIIA sPLA$_2$, in said blood sample from said subject compared respectively to the reference serum concentration of GIIF, GV and/or GIIA sPLA$_2$s in subjects not infected with *Plasmodium*, is further indicative that said subject is infected with *Plasmodium* with low parasitaemia.

As used herein, "low parasitaemia" refers to a parasitaemia inferior to 0.5%, meaning a number of *Plasmodium*-infected red blood cells inferior to 0.5 per 100 total red blood cells of blood from said subject (Warhurst and Williams, 1996).

To determine the percentage of malaria parasitaemia, malaria parasite-infected red cells are routinely counted against 1,000 erythrocytes from blood smears.

In another preferred embodiment, a superior serum concentration of GIIF and/or GV sPLA$_2$s, preferably GIIF and GV sPLA$_2$s, and optionally in addition GIIA sPLA$_2$, in said blood sample from said subject compared respectively to the reference serum concentration of GIIF, GV and/or GIIA sPLA$_2$s in subjects not infected with *Plasmodium*, is further indicative that said subject is in remission (i.e., the parasitaemia is decreasing).

By way of example, said remission can be consecutive to a malaria treatment of said subject.

Usually, the serum concentrations of GIIF, GV and GX sPLA$_2$s in a healthy human (i.e., not infected with *Plasmodium*) are below their detection limits when the method TR-FIA is used for the detection, i.e., respectively 4 µg/L, 11 µg/L and 2 µg/L, and the serum concentration of GIIA is <10 µg/L (Nevalainen et al., 2005).

In a preferred embodiment of the method of the present invention carried out in a human, a serum concentration of GIIF sPLA$_2$ superior to 4 µg/L, and/or a serum concentration of GV sPLA$_2$ superior to 11 µg/L and/or a serum concentration of GX sPLA$_2$ superior to 2 µg/L, and optionally in addition a serum concentration of GIIA sPLA$_2$ superior to 10 µg/L, e.g., measured by immunoassay, preferably by TR-FIA, is indicative that said subject is infected with *Plasmodium* as defined above.

In another preferred embodiment of the method of the present invention, a serum concentration of GIIF sPLA$_2$ and/or a serum concentration of GV sPLA$_2$ and/or a serum concentration of GX sPLA$_2$ respectively superior to 7, 20 and 4 µg/L and optionally in addition a serum concentration of GIIA sPLA$_2$ respectively superior to 15 µg/L, and by order of increasing preference, respectively superior to 20 µg/L, respectively superior to 50 µg/L or respectively superior to 100 µg/L, in a human, e.g., measured by immunoassay, preferably by TR-FIA, is indicative that said human is infected with *Plasmodium*, preferably with *P. falciparum*, as defined above.

The present invention also relates to a kit for diagnosing a *Plasmodium* infection, preferably a *P. falciparum* infection, in a subject, preferably a human, comprising:
  antibodies directed against a mammal GIIF sPLA$_2$, preferably the human GIIF sPLA$_2$, antibodies directed against a mammal GV sPLA$_2$, preferably the human GV sPLA$_2$ and/or antibodies directed against a mammal GX sPLA$_2$, preferably the human GX sPLA$_2$,
  optionally, antibodies directed against a mammal GIIA sPLA$_2$, preferably the human GIIA sPLA$_2$,
  at least one positive control, preferably a reference serum or blood sample from a *Plasmodium* infected mammal, preferably a *P. falciparum* infected mammal, and
  at least one negative control, preferably a reference serum or blood sample from a mammal non-infected with *Plasmodium*, preferably *P. falciparum*.

In a preferred embodiment of said kit, it comprises antibodies directed against a mammal (e.g., human) GIIF sPLA$_2$ and antibodies directed against a mammal (e.g., human) GX sPLA$_2$.

In another preferred embodiment of said kit, it comprises antibodies directed against a mammal (e.g., human) GIIF sPLA$_2$ and antibodies directed against a mammal (e.g., human) GV sPLA$_2$.

In another preferred embodiment of said kit, it comprises antibodies directed against a mammal (e.g., human) GIIF sPLA$_2$ and antibodies directed against a mammal (e.g., human) GIIA sPLA$_2$.

Antibodies directed against GIIA, GIIF, GV and GX sPLA$_2$s of a given mammal (e.g., human) may be obtained using methods known to those skilled in the art, including immunizing a non-human mammal, preferably a rabbit, rat or mouse with recombinant GIIA, GIIF, GV and GX sPLA$_2$s from said given mammal (e.g., human).

The term "recombinant" refers to the use of genetic engineering methods (cloning, amplification) to produce said GIIA, GIIF, GV and GX sPLA$_2$s. Recombinant mammal GIIA, GIIF, GV and GX sPLA$_2$s can be prepared using methods known to those skilled in the art. By way of example, recombinant human or mouse GIIA, GIIF, GV and GX sPLA$_2$s can be prepared as described in Singer et al., 2002.

The invention also relates to the use of an antibody directed against a mammal, preferably human, GIIF sPLA$_2$, GV sPLA$_2$ and/or GX sPLA$_2$, and optionally in addition an antibody directed against a mammal GIIA sPLA$_2$, for an in vitro diagnostic of an infection with *Plasmodium*, preferably *P. falciparum*, in a subject.

The present invention also relates to a recombinant mammal sPLA$_2$ selected from the group consisting of GIIF, GV and GX sPLA$_2$s, preferably GIIF and GX sPLA$_2$s, and most preferably GX sPLA$_2$, for use for treating or preventing malaria, preferably *P. falciparum* malaria.

The present invention also relates to a pharmaceutical composition comprising at least two recombinant mammal sPLA$_2$s selected from the group consisting of GIIA, GIIF, GV and GX sPLA$_2$s, for simultaneous, separate or sequential use in the treatment or prevention of malaria.

The present invention also relates to the use of a recombinant mammal sPLA$_2$ selected from the group consisting of GIIF, GV and GX sPLA$_2$s, preferably GIIF and GX sPLA$_2$s, and most preferably GX sPLA$_2$, for the preparation of a medicament for treating or preventing malaria, preferably *P. falciparum* malaria.

In a preferred embodiment of this aspect of the present invention, said mammal is a human or a mouse, preferably a human.

As used herein, the term "treating" refers to the administration of a recombinant mammal GIIA, GIIF, GV and/or GX sPLA$_2$s, to a patient who has malaria or a symptom of malaria, preferably *P. falciparum* malaria, with the purpose to cure, heal, alleviate, relieve, alter, remedy, ameliorate, improve, or affect the disease or the symptoms of said disease.

As used herein, the term "preventing" refers to the reduction or the inhibition of a risk of malaria, preferably *P. falciparum* malaria, in a subject not suffering from malaria, or that the onset of the malaria is delayed or eliminated, in a subject having been exposed to (i.e., in contact with) a *Plasmodium*.

The present invention also provides a method of treating or preventing malaria, preferably *P. falciparum* malaria, in a subject, comprising administering a recombinant mammal GIIF, GV and/or GX sPLA$_2$s as defined above to said subject in need thereof.

To improve the efficacy of said sPLA$_2$s, these sPLA$_2$s can be combined to PAF (platelet-activating factor).

The present invention also relates to a pharmaceutical composition comprising the platelet-activating factor (PAF) and at least one recombinant mammal phospholipase A2 selected from the group consisting of GIIA, GIIF, GV and GX sPLA$_2$s, preferably GX sPLA$_2$.

The pharmaceutical composition as defined above can also comprise a pharmaceutically acceptable carrier.

As used herein, the expression "pharmaceutically acceptable carrier" refers to any and all solvents, adjuvant, excipient, dispersion media, coatings, antibacterial and antifungal agents, isotonic and absorption delaying agents, and the like, compatible with pharmaceutical administration. Suitable carriers are described in the most recent edition of Remington's Pharmaceutical Sciences, a standard reference text in the field. The use of such media and agents for pharmaceutically active substances is well known in the art.

The present invention also relates to a pharmaceutical composition comprising the platelet-activating factor (PAF) and at least one recombinant mammal phospholipase A2 selected from the group consisting of GIIA, GIIF, GV and GX sPLA$_2$s, for simultaneous, separate or sequential use in the treatment or prevention of malaria, preferably *P. falciparum* malaria.

The present invention also relates to the use of a recombinant mammal GIIF, GV or GX sPLA$_2$, preferably from human origin, to screen, in vitro or in non-human mammals, for compounds (e.g., drugs) that inhibit or reduce the development of *Plasmodium*, preferably *P. falciparum*.

By way of example, it can involve contacting a candidate compound with a red blood cell or serum and then determining any modulatory (inhibition or reduction) effect on the development of *Plasmodium* resulting from said candidate compound compared to said recombinant mammal GIIF, GV or GX sPLA$_2$s.

BRIEF DESCRIPTION OF THE DRAWINGS

In addition to the preceding features, the invention further comprises other features which will emerge from the following description, which refers to examples illustrating the present invention, as well as to the appended figures.

DETAILED DESCRIPTION

Example 1

Figure 1:
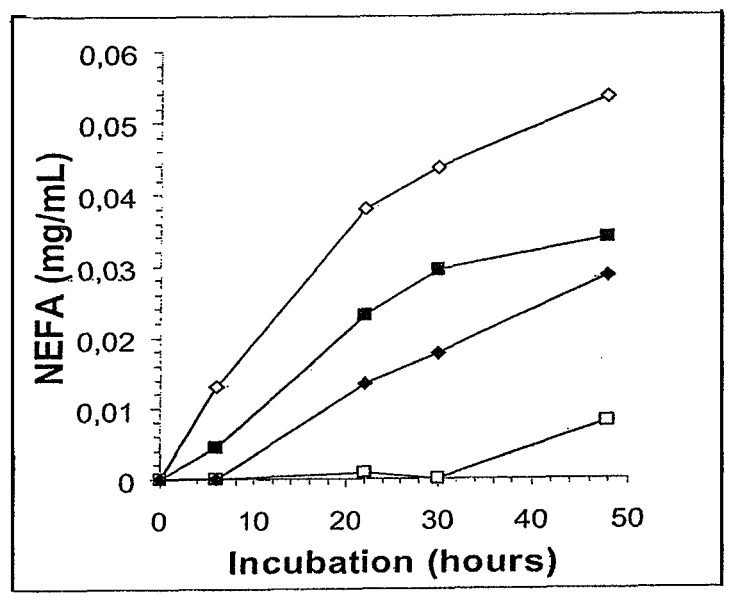
FIG. 1 shows the enzymatic hydrolysis of human plasma by GX sPLA$_2$. Crude human plasma was incubated with 3 nM of recombinant human GX sPLA$_2$ (◊), 15 nM of the full length (■) or truncated (□) recombinant human GIIF sPLA$_2$, and 15 pM of the bee venom sPLA$_2$ (♦), for 48 h at 37° C. Aliquots were taken at times 0 h, 6 h, 22 h, 30 h and 48 h of incubation. NEFAs in each aliquot were measured using the NEFA-C kit (WAKO)

Evaluation of Anti-*Plasmodium* Activities of the Human sPLA$_2$s

1) Materials and Methods
  1.1) Materials
  Purified recombinant human sPLA$_2$s were prepared as described in Singer et al. (2002). The accession number in the GenBank database of the mRNA encoding the different sPLA$_2$s are given below:

| Recombinant human sPLA2 groups: | GenBank accession number or Reference: |
|---|---|
| IB | gi\|38016927 |
| IIA | gi\|239915981 |
| IID | gi\|21314652 |
| IIE | gi\|7657460 |
| IIF (full length) | gi\|145553988 |
| IIFΔC (IIF lacking the C-terminal 23-amino acid extension) | Singer et al., 2002 |
| III | gi\|142976883 |
| V | gi\|113722111 |
| X | gi\|4505844 |
| XIIA | gi\|195539345 |
| XIIB | gi\|45505134 |

*Apis mellifera* (bee) venom sPLA$_2$, *Naja mossambica mossambica* venom sPLA$_2$ and high quality grade biochemical reagents used throughout this work were purchased from Sigma (St Quentin Fallavier, France). Plasmion was from Fresenius Kabi France (Sèvres, France). Albumax II® was from Invitrogen (Cergy Pontoise, France).

NEFA-C kit and Phospholipids B kit used for quantitative determination of non-esterified fatty acids (NEFAs) and phospholipids (PLs) respectively were from WAKO Chemicals GmbH (Neuss, Germany). 3H-hypoxanthine (37 MBq/mL) was from GE Healthcare (France). Diff-Quick® stain was purchased from Medion Diagnostics GmbH (Düdingen, Switzerland). LY329722 (sodium [3-aminooxalyl-1-benzyl-2-ethyl-6-methyl-1H-indol-4-yloxy]-acetic acid) (Smart et al., 2006).

1.2) Methods
 1.2.1) Culture and Synchronization of *P. falciparum*
 The chloroquine-resistant *P. falciparum* FcB1/Colombian strain was used. Under the following culture conditions, the in vitro life cycle of the FcB1 strain was 48 hours. Cultures were grown in complete medium consisting of RPMI 1640 (Life Technologies, Inc.) supplemented with 11 mM glucose, 27.5 mM NaHCO3, 100 UI/mL penicillin, 100 µg/mL streptomycin, adjusted to pH 7.4 before addition of heat-inactivated human serum (A+ blood group, 8% final) or Albumax II® (0.5% final), according to the procedure of Trager and Jensen (1976). Parasites were routinely grown at 37° C. in human A+ RBCs (Red blood cells) at a 2% haematocrit and 2-6% parasitemia, in a 3% CO2, 6% O2 and 91% N2 atmosphere. Semi-synchronized cultures were established by Sorbitol (Lambros) treatment. Highly synchronized cultures (4 hour-window synchronization) were obtained by successive Plasmion (Pasvol) and Sorbitol treatments. Parasitaemia and stage distribution were determined by optical examination of Diff-Quick stained culture smears. Parasitaemia (expressed in percent) is hundred times the number of parasitized erythrocytes divided by the total number of erythrocytes.

1.2.2) Enzymatic Activity Assay on *E. coli* Membranes
Recombinant sPLA$_2$s were routinely checked for enzymatic activity through hydrolysis of autoclaved $^3$H-oleic acid-labelled *E. coli* (Franson et al., 1974).

1.2.3) Anti-*Plasmodium* Activity Assay (Dose-Response Assay)
Dried preparations of the purified recombinant human sPLA$_2$s were re-suspended at high concentration (usually 50 µM) in RPMI 0.05% BSA, and then tested individually for their capacity to inhibit the in vitro intra-erythrocytic development of *P. falciparum*. Dose-response assays based on $^3$H-hypoxanthine incorporation by growing parasites were performed as in Guillaume et al. (2004). Radioactivity was measured with a 1450 Microbeta counter (Wallac, Perkin Elmer). Percentage of growth inhibition was calculated from the parasite-associated radioactivity compared with control without sPLA$_2$. Values for the IC$_{50}$ were determined from dose-response curves.

1.2.4) Purification and Minimal Oxidation of the Lipoprotein fractions

Purification, oxidation and enzymatic hydrolysis procedures were performed under sterile conditions. Non-fasted human plasma was aliquoted and frozen at −20° C. just after blood drawing. Three weeks before enzymatic hydrolysis experiment, one aliquot of plasma was thawed for purification of CM (chylomicrons)/VLDL (very low-density lipoprotein), LDL (low-density lipoprotein) and HDL (high-density lipoprotein) fractions by differential centrifugation, according to the procedure described in Havel et al. (1955). The lipoprotein fractions were extensively dialyzed at 4° C. against phosphate-buffered saline (PBS: 0.15 M NaCl, 10 mM sodium phosphate buffer, pH 7.2).

To prepare minimally oxidized lipoproteins, air/light oxidation was induced by storage of the fractions in a transparent flask at ambient temperature and under sterile air exchange for 18-20 days.

Native lipoproteins were prepared from another aliquot of the plasma just prior to the hydrolysis assay. When necessary, the lipoprotein fractions were stored at 4° C. under N$_2$ atmosphere and in the dark after addition of 50 µg/mL gentamycin.

Phosphatidylcholine (PC) content of each lipoprotein fraction was measured by the use of the Phospholipid B dosage kit (WAKO Chemicals), following manufacturer's instructions.

1.2.5) Evaluation of the Oxidized Lipoproteins Anti-*Plasmodium* Toxicity

Decreasing concentrations of each native and oxidized lipoprotein fraction were tested following procedure of the dose-response assay as described above. Positive control for the parasite growth was without lipoprotein.

1.2.6) Plasma and Lipoprotein Lipolysis by sPLA$_2$s a) Specific Activities of sPLA$_2$s on Plasma:

Kinetic analysis of human plasma hydrolysis by sPLA$_2$s was performed by mixing on ice 50 µL of crude plasma with recombinant sPLA$_2$s at various final concentrations (respectively 2×, 5× and 10× the IC$_{50}$ value). At time zero, the mixture was transferred to 37° C. Samples (7 µL) were taken after 5, 15, 30 and 60 minutes of incubation and quickly frozen at −20° C. An aliquot of plasma without enzyme was similarly processed. Concentration of non-esterified fatty acids (NEFAs) in each sample was measured by a discontinuous enzymatic method using the NEFA-C test kit from WAKO, following manufacturer's instructions. The amount of NEFAs in each enzyme-containing plasma sample was subtracted for NEFAs in enzyme-free plasma sample. Specific activity for each of the sPLA$_2$s was determined from the linear part of the curve [NEFA]=f(t). Experiment was repeated three times with plasmas from different donors and different batches of sPLA$_2$s.

b) 48 h-Hydrolysis of Plasma

Crude human plasma was incubated with 3 nM of recombinant human GX sPLA$_2$, 15 nM of the full length or the truncated form (IIFΔC) of recombinant human GIIF sPLA$_2$, and 15 pM of the bee venom sPLA$_2$, for 48 h at 37° C. Aliquots (7 µL) were taken at times 0 h, 6 h, 22 h, 30 h and 48 h of incubation. NEFAs were measured in each aliquot by using the NEFA-C kit (WAKO). Experiment was repeated twice with different plasmas.

c) Enzymatic Hydrolysis of Purified Lipoproteins

Plasma and purified LDL and HDL were adjusted to 1.67 mg phospholipid (PL)/mL final concentration in PBS. Because purification yielded low amount of CM/VLDL, the CM/VLDL fraction was adjusted to 1.00 mg PL/mL. CaCl$_2$ (1 mM final) was added to the lipoprotein fractions. 200 µL of each fraction were deposited in a 96-well plate and incubated for 15 hours at 37° C., alone or in the presence of recombinant human GX sPLA$_2$ (hGX PLA$_2$, 25.0 nM), recombinant human GIIF sPLA$_2$ (hGIIF PLA$_2$, 125.0 nM), bee venom sPLA$_2$ (bvPLA$_2$, 0.18 nM) and *Naja mossambica mossambica* venom sPLA$_2$ (*Naja* PLA$_2$, 0.05 nM). NEFAs were measured in triplicate using the NEFA-C kit (WAKO). Value from each fraction was normalized by subtracting the NEFA amount in the corresponding fraction without enzyme. Two independent experiments with lipoproteins from different plasmas were performed, which gave similar qualitative results. According to the experiment, maximum hydrolysis reached 50% or 65% of total PLs in the fraction.

1.2.7) Involvement of Enzymatic Activity in GX sPLA2-Induced Inhibition of Parasite Growth A schizont-enriched culture of *P. falciparum* was grown for 24 h in the presence of 50 nM recombinant human GX sPLA$_2$, or 50 nM GX sPLA$_2$ plus 37.5 µM LY329722, a potent inhibitor of the GX sPLA$_2$ enzymatic activity (75 nM IC$_{50}$, Smart et al., 2006); controls in normal culture conditions and in the presence of LY329722 alone (LY) were processed in parallel. Parasitaemia (%) before incubation, and after 24 h of incubation, was determined from Diff Quick-stained smears. Parasite growth was expressed as the percent delta of parasitaemia, using the following formula:

$$\Delta P=[(P_x-P_0)/(P_{100}-P_0)]\times 100;$$ where $\Delta P$ is in percent, $P_0$ is the parasitaemia (%) in the initial culture, $P_{100}$ is the parasitaemia (%) after 24 h in normal culture conditions, and $P_x$ is the parasitaemia (%) after 24 h in experimental conditions.

1.2.8) Sensitivity of the *P. falciparum* Blood Stages to GX sPLA$_2$

A parasite culture was synchronised on a 4 h-window. Parasites aged 0-4 h post-invasion (rings), 18-22 h post-invasion (trophozoites), and 34-38 h post-invasion (schizonts) were adjusted to 1% parasitaemia and 2% haematocrit in complete medium, and were then incubated in a 96-well plate in a candle jar at 37° C., with or without 100 nM of recombinant GX sPLA2. After 15 hours, cells were centrifuged at 900×g for 2 min, washed in RPMI and re-suspended at a 2% haematocrit in fresh complete medium for further growth. When re-invasion had occurred (*P. falciparum* invades new RBCs when its 48 hour-development cycle is completed), parasitaemia (%) in each well was determined from Diff Quick-stained smears. GX sPLA$_2$ inhibitory activity on the complete parasite cycle was assessed by incubating rings with the recombinant enzyme for 48 hours.

1.2.9) GX sPLA$_2$ Lipolysis of Infected Red Blood Cells a) Determination of Phosphatidylcholine (PC) Content in Erythrocytes and Plasma 100 µL it of packed non-infected RBCs (1.1×10$^9$ RBCs) were washed in PBS at room temperature, then lysed in 10 volumes of iced 5P8 buffer (5 mM sodium phosphate, ph 8.0) and centrifuged at ×14.000 g for 15 minutes at 4° C. Pelleted ghosts were washed several times in iced 5P8 to fully remove haemoglobin, and re-suspended in 5P8 to the initial RBC volume (100 µL). Phospholipids (PC) in ghosts were measured by using the phospholipids B kit from WAKO, following manufacturer's instructions. PC content was also measured in crude plasma. From at least four independent measurements (erythrocytes and plasma from different donors), PC content was estimated at 1.45 g/L (volume of packed erythrocytes) in RBCs and 2.20 g/L in plasma.

b) Enzymatic Treatment of Infected RBCs
i) Hydrolysis of Young and Mature Stages:

A parasite culture was enriched in young parasite stages (rings+early trophozoites) by sorbitol treatment. Parasitaemia (2.5-3%) and stage distribution were determined from Diff-Quick staining of culture smears. One half of the culture was processed immediately as described below. The other half was maintained in normal culture conditions for a further 24 hour-period for the parasite to reach the schizont stage, and then the culture was processed similarly. Erythrocytes were centrifuged for 2 minutes at ×900 g. One volume (100 µL) of packed erythrocytes was washed in RPMI and re-suspended in 1 vol. of RPMI BSA 0.05%. 50 µL of the suspension were distributed into 3 wells of a 96-well microplate. Non-infected erythrocytes which had been maintained in culture conditions for 24 h prior to the experiment were processed similarly. 25 µL volumes of plasma diluted ×4.4 in RPMI were also distributed into wells. A maximum 2 µL volume of recombinant GX sPLA$_2$ and bee venom sPLA$_2$ in PBS BSA 0.02% were added to respectively 30 nM and 0.2 nM final concentrations. Control wells for endogenous generation of NEFAs were without enzyme. The microplate was incubated in a candle jar for 5 hours at 37° C. Plasma samples and cell supernatants were taken and frozen at −20° C. Ghosts were prepared from pelleted erythrocytes and frozen at −20° C. Samples were thawed on ice just prior to triplicate measurement of NEFAs using the NEFA-C kit from WAKO. NEFAs in erythrocyte samples are expressed as the sum of NEFAs from ghosts and corresponding supernatant.

ii) Hydrolysis of Serum-Derived and Albumax II® Derived Parasite Cultures:

Parasites were grown for several cycles in culture medium supplemented either with 8% human serum or with 0.5% Albumax II®. Cultures were semi-synchronized by Sorbitol treatment 2-3 days prior to the experiment. When they contained mainly mature parasites and had reached 2.5-3% parasitaemia, cells from both cultures were washed in RPMI, re-suspended in RPMI 0.05% BSA at a 50% haematocrit, and distributed in wells of a 96-well microplate in the presence or absence of 50 nM of recombinant GX sPLA2. The microplate was incubated at 37° C. for 6 h in a candle jar. Incubations of non-infected RBCs and serum were performed in parallel as respectively negative and positive controls of the GX sPLA$_2$ activity. Supernatants were taken and ghosts were prepared from cells. NEFAs were measured using the NEFA-C kit (WAKO). Values for healthy RBCs (RBC) and infected cultures (iRBC) are the sum of NEFAs from paired ghosts and supernatants.

1.2.10) Evaluation of the In Vitro Chemosensitizing Activity of Platelet-Activating Factor (PAF)

Quantitative analysis of the increased activity of recombinant hGX sPLA$_2$ when combined with PAF was done by comparing concentration-response curves for hGX sPLA$_2$ alone and in the presence of several fixed, sub-inhibitory concentrations of PAF. Effects of each fixed concentration of PAF on the response of the parasites (IC$_{50}$) to hGX sPLA$_2$ were expressed as the response modification index (RMI) (Oduola et al., 1998). The RMI was calculated by the following formula: RMI=IC$_{50}$(A,B)/IC$_{50}$(A), where drug A is hGX sPLA$_2$ and B is PAF. An RMI of 1.0 represents no change in the IC$_{50}$ for the recombinant hGX sPLA$_2$ combined with PAF. The RMI values<1.0 represent chemosensitization (including possible synergy). Sub-inhibitory concentrations of PAF in the assay were: 25 μM, 37.5 μM and 50 μM.

2) Results 2.1) Anti-*Plasmodium* Activities of Human $sPLA_2$s

Recombinant human $sPLA_2$s from groups IB, IIA, IID, IIE, IIF, III, V, X, XIIA and XIIB were assayed for inhibition of the *P. falciparum* development in vitro. Results are shown in Table I below.

Table I:

Anti-*P. falciparum* activities of human $sPLA_2$s. $IC_{50}$ values are the mean of independent dose-response assays using human red blood cells and serum from different donors for the *P. falciparum* culture. At least two assays were performed with the GIB, GIIA, GIID, GIIE, GIII, GXIIA and GXIIB non-toxic $sPLA_2$s. $IC_{50}$ values for GX and GIIF $sPLA_2$s are the mean of four independent determinations.

| sPLA2 group | IB | IIA | IID | IIE | IIF | IIFΔC | III | V | X | XIIA | XIIB |
|---|---|---|---|---|---|---|---|---|---|---|---|
| $IC_{50}$ ± SD (nM) | >1250 | >1250 | >250 | >250 | 14.3 ± 10.4 | >250 | ±250 | 162.5 ± 90.9 | 2.9 ± 2.4 | >250 | >250 |

Group-X and -IIF enzymes were found inhibitory, with $IC_{50}$ values of 2.9±2.4 nM and 14.3±10.4 nM, respectively. Group-V $sPLA_2$ exhibited a low inhibitory activity, with $IC_{50}$ values of 162.5±90.9. Remarkably, the inflammatory $sPLA_2$, i.e. GIIA $sPLA_2$, whose level has been shown to increase in the plasma of malaria patients, was clearly inactive against the parasite.

Group-IIF $sPLA_2$ is structurally unique among $sPLA_2$s, in that it has an unusually long, proline-rich C-terminal extension (Valentin et al., 2000b). This extension mediates the GIIF $sPLA_2$ binding to mammalian cells (Wijewickrama et al., 2006). By contrast to the full length form, the C-terminus truncated form of GIIF $sPLA_2$ (GIIFΔC), although catalytically active (Singer et al., 2002), did not inhibit *Plasmodium*, suggesting that the attachment of truncated GIIF $sPLA_2$ to the erythrocyte membrane and/or lipoprotein surface might be impaired, leading to a drop in toxicity.

2.2) Human $sPLA_2$s' Activities on Serum Components 2.2.1) Anti-*Plasmodium* Activities of Human $sPLA_2$s are Lowered in the Absence of Serum The toxicity of venom $sPLA_2$s toward *P. falciparum* has been attributed mainly to enzymatic hydrolysis of serum phospholipids because those $sPLA_2$s are largely inefficient at killing *P. falciparum* in the presence of Albumax II®, a phospholipid-poor serum substitute (Guillaume et al., 2004). Anti-*Plasmodium* activities of GX and GIIF $sPLA_2$s were thus assayed in Albumax II® to assess for their requirement in exogenous PLs. $IC_{50}$ values of both enzymes were found to increase in Albumax II®. Group-X $sPLA_2$ $IC_{50}$ value exhibited variable increase according to the experiment, ranging from 25-fold to 150-fold its value in serum. GIIF $sPLA_2$ $IC_{50}$ value was increased by approximately 17.5-fold. Therefore, toxicities of both GX and GIIF $sPLA_2$s appeared to be lowered in the presence of Albumax II®, suggesting that their mechanisms of action rely to some extent on the presence of extra-cellular PLs.

2.2.2) Enzymatic Activity on Human Plasma Hydrolysis of serum by human sPLA$_2$s has been reported for GV and GIIA sPLA$_2$s: the GV sPLA$_2$ was found active, the GIIA sPLA$_2$ was found inactive (Rosengren et al., 2006). The specific activities of GX, GIIF and GV sPLA$_2$s on whole human plasma was determined by measuring NEFAs released upon incubation with different enzyme concentrations and incubation times. Activities of the bee (*Apis mellifera*) and *Naja mossambica mossambica* venom sPLA$_2$s (respectively bvPLA$_2$ and *Naja* PLA$_2$) were measured for comparison. Results are shown in Table II.

Table II:

Specific activities of sPLA$_2$s on human plasma. Hydrolysis of plasma phospholipids by human and venom sPLA$_2$s was assayed using different incubation times and enzymes concentrations. Hydrolysis was assessed by measuring the amount of NEFAs in samples using the colorimetric assay developed by WAKO (NEFA-C kit). Enzymatic production of NEFAs was corrected for endogenous production of NEFAs measured in the absence of sPLA2. Specific activity for each of the sPLA$_2$s was determined from the linear part of the kinetic curve. Values are the mean of three independent experiments. SD: standard deviation. Anti-*P. falciparum* activities (IC$_{50}$) of the respective sPLA$_2$s are given for comparison.

| sPLA2 | hGX | hGIIF | hGV | bvPLA2 | Naja PLA2 |
|---|---|---|---|---|---|
| Specific activity ± SD (μmol NEFA/min × mg enzyme) | 8.23 ± 0.92 | 0.92 ± 0.30 | 0.33 ± 0.09 | 515.36 ± 72.52 | 674.68 ± 77.51 |
| IC$_{50}$ (nM) | 2.9 ± 2.4 | 14.3 ± 13.4 | 162.5 ± 90.9 | 0.015 ± 0.009 | 0.003 ± 0.002 |

Human enzymes exhibited lower activities on plasma than venom enzymes. Among the human sPLA$_2$s, GX sPLA$_2$ was 9-times and 30-times more active than GIIF and GV sPLA$_2$s, respectively. In line with what has been reported in serum, high concentration (1 μM) of GIIA sPLA$_2$ was inefficient at hydrolysing plasma (not shown). Of note, sPLA$_2$s' activities in plasma are in line with their toxic properties against *P. falciparum*, indicated by their IC$_{50}$ values.

NEFAs released from plasma by IC$_{50}$ concentrations of GX, GIIF and bee venom sPLA$_2$s were measured on a time scale relevant to the dose-response assay, i.e. 48 h. Three independent experiments with plasmas from different donors were performed that gave similar qualitative results. Results from one experiment are presented in FIG. 1. Each sPLA$_2$ at its IC$_{50}$ concentration hydrolysed plasma at constant rate for at least 20 h, with GX sPLA$_2$ being the most active. This indicated that in the presence of the human sPLA$_2$s, the parasite is potentially submitted to continuous release of NEFAs and lysophospholipids, most probably at the origin of toxicity, as proven in the case of the bee venom enzyme. The non toxic, truncated form of GIIF sPLA$_2$ was largely inefficient at hydrolysing plasma, reinforcing the idea that hydrolysis of PLs is involved in the anti-*Plasmodium* activity of native GIIF sPLA2.

2.2.3) Lipoprotein Hydrolysis by GX and GIIF sPLA$_2$s

GIIA, GIIF, GV and GX sPLA$_2$s are known to readily hydrolyse purified LDL and HDL in their native state (Ishimoto, et al, 2003; Pruzanski et al., 2005, Sato et al., 2008), although GIIA sPLA$_2$ was found less efficient than the other sPLA$_2$s (Gesquiere et al., 2002). Malaria patients exhibit elevated oxidation of lipoproteins as compared to normal subjects (Sibmooh et al., 2004), and it is known that such modifications can modulate the susceptibility of lipoproteins to sPLA$_2$s (Eckey et al., 1997; Pruzanski et al., 1998). The ability of recombinant GX and GIIF sPLA$_2$s to hydrolyse oxidized lipoproteins in vitro was then analysed.

Prior to the experiment, because it was also previously reported (Guillaume et al., 2006) that CM/VLDL oxidized by prolonged exposure to air and light (minimally oxidized lipoproteins) are inhibitory to the development of *P. falciparum* in vitro, it was analysed whether similarly oxidized LDL and HDL would be toxic as well.

Figure 2:
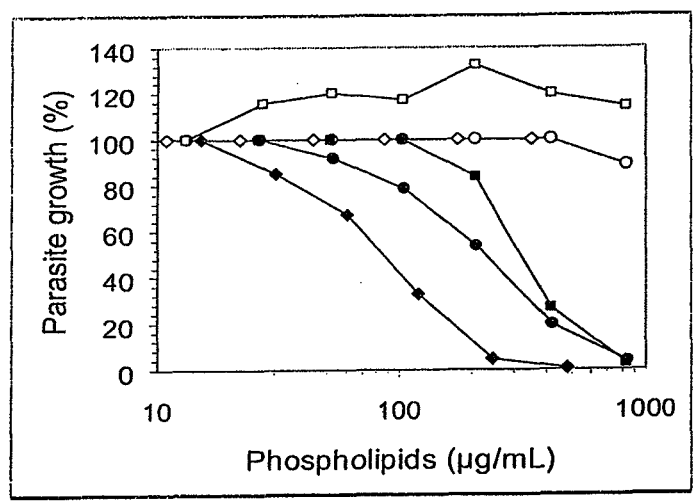
FIG. 2 shows the anti-*Plasmodium* toxicity of oxidized lipoproteins. Purified lipoproteins in native state or after air-light oxidation were assayed for anti-*Plasmodium* toxicity. An asynchronous culture of chloroquine-resistant *P. falciparum* FcB1/Colombian strain (1% parasitaemia, 2% haematocrit) was grown in the presence of decreasing concentrations of each lipoprotein preparation. Parasite growth was assessed by [$^3$H]-hypoxanthine incorporation into nucleic acids. Native CM/VLDL (◊), oxidized CM/VLDL (♦); native LDL (○), oxidized LDL (●); native HDL (□), oxidized HDL (■)

Results are shown in FIG. 2. It can be seen that all three classes of lipoproteins are inhibitory when oxidized, with respective IC$_{50}$ values of 85 μg PL/mL (CM/VLDL), 200 μg PL/mL (LDL), and 300 μg/PL/mL (HDL). Noticeably, parasite growth was enhanced in the presence of native HDL, confirming the nutrient properties of this particular lipoprotein (Grellier et al., 1990).

Assuming that PC is the major phospholipid in either class of lipoproteins, enzymatic hydrolysis of lipoproteins was performed at a given enzyme-to-PC ratio after PC measurement in lipoproteins. The bee and *Naja* venom sPLA$_2$s were assayed in parallel to the human enzymes. Each sPLA$_2$ was used at approximately 10×IC$_{50}$. Experiment was performed twice with lipoproteins from different donors and gave similar qualitative results.

Figure 3:
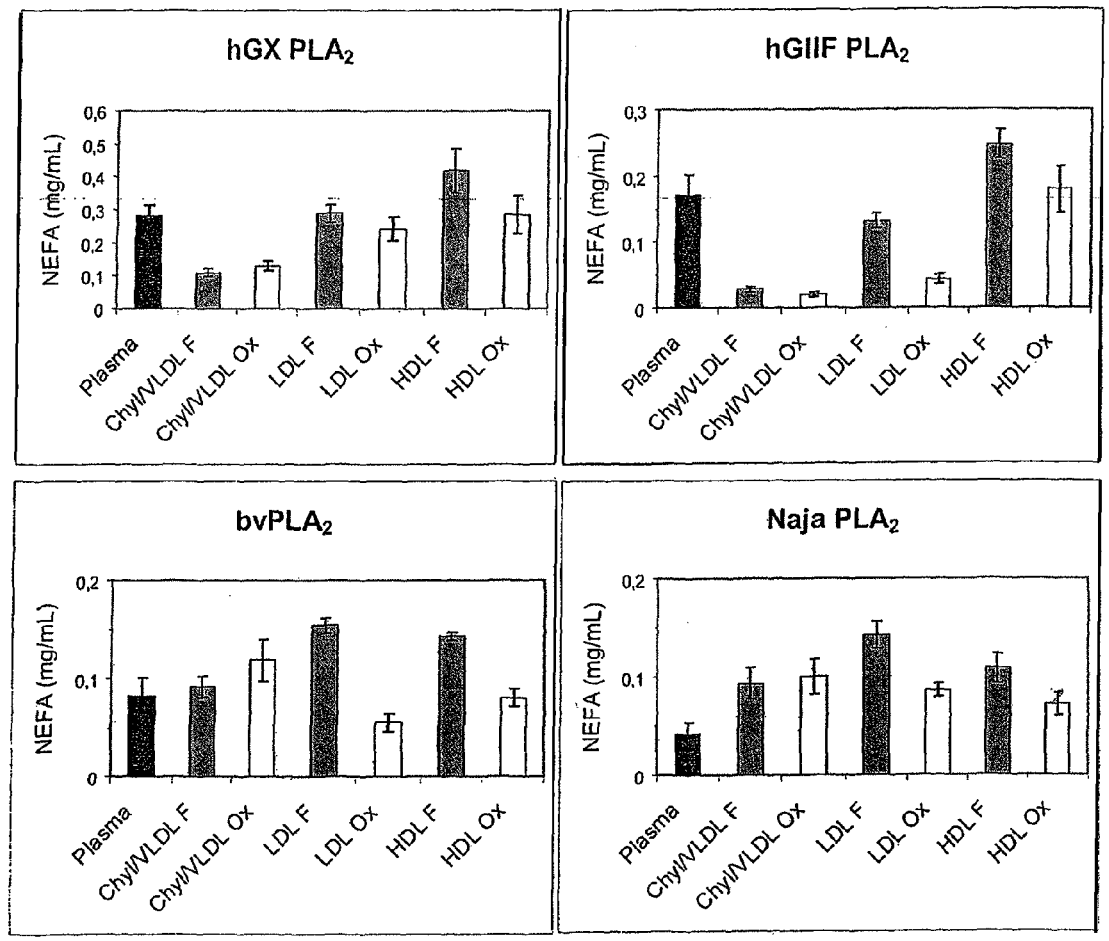
FIG. 3 shows the lipoprotein hydrolysis by GX and GIIF sPLA$_2$s, compared with venom sPLA$_2$s. CM/VLDL, LDL and HDL were purified from human plasma and used either fresh (F) or after minimal oxidization by air and light (Ox). After phospholipid content determination, plasma, LDL and HDL were adjusted to 1.6 mg PL/mL final concentration in PBS calcium. Because low amount was available, the CM/VLDL fraction was adjusted to 1.0 mg PL/mL. Each sample was incubated for 15 hours at 37° C., alone or in the presence of recombinant human GX sPLA$_2$ (hGX PLA$_2$; 25 nM), recombinant human GIIF sPLA$_2$ (hGIIF PLA$_2$; 125 nM), bee venom sPLA$_2$ (bvPLA$_2$; 0.18 nM) and *Naja mossambica mossambica* venom sPLA$_2$ (*Naja* PLA$_2$; 0.05 nM). NEFAs were quantified using the NEFA-C kit (WAKO). Values are the mean±SD of triplicate measurements. They were normalized by subtracting NEFA amount in the absence of enzyme. Two independent experiments with lipoproteins from different plasmas were performed, which gave similar qualitative results. Results from one experiment are shown.

Results from one experiment in triplicate are shown in FIG. 3:

the group-X enzyme hydrolysed lipoproteins in the preferential order HDL>LDL>CM/VLDL;

group-IIF sPLA$_2$ hydrolysed lipoproteins in the same preferential order than GX sPLA$_2$, but, unlike GX sPLA$_2$, it hydrolysed poorly the triglyceride-rich lipoproteins (CM/VLDL);

contrasting with the human sPLA$_2$s, the bee and *Naja* enzymes hydrolysed lipoproteins in the following preferential order: LDL>HDL>CM/VLDL.

except in the case of the triglyceride (TG)-rich lipoproteins, substantial amount of NEFAs was generated by either enzyme from the oxidized lipoproteins. However, it was noticed that the amount was smaller than that generated from the lipoproteins in their native state.

2.3) Properties of the Anti-*Plasmodium* hGX sPLA$_2$ 2.3.1) The Catalytic Activity of GX sPLA$_2$ is Involved in the Anti-*Plasmodium* Mechanism Inhibition of parasite growth was removed in the presence of LY329722, a potent inhibitor of the recombinant GX sPLA$_2$ (Smart et al., 2006) (FIG. 4A), establishing the prevalence of enzymatic activity in the anti-*Plasmodium* activity of GX sPLA2. In accordance with this, high concentrations of the catalytically inactive H48Q mutant of GX sPLA$_2$ inhibited poorly the *P. falciparum* development (30% inhibition at 1.25 μM). Insofar as the H48Q mutant exhibits unaffected interfacial binding capacities, this confirmed that phospholipid hydrolysis is essential to the GX sPLA$_2$ toxic mechanism.

2.3.2) All Blood Stages of *P. falciparum* are Sensitive to GX sPLA$_2$.

Figure 4:
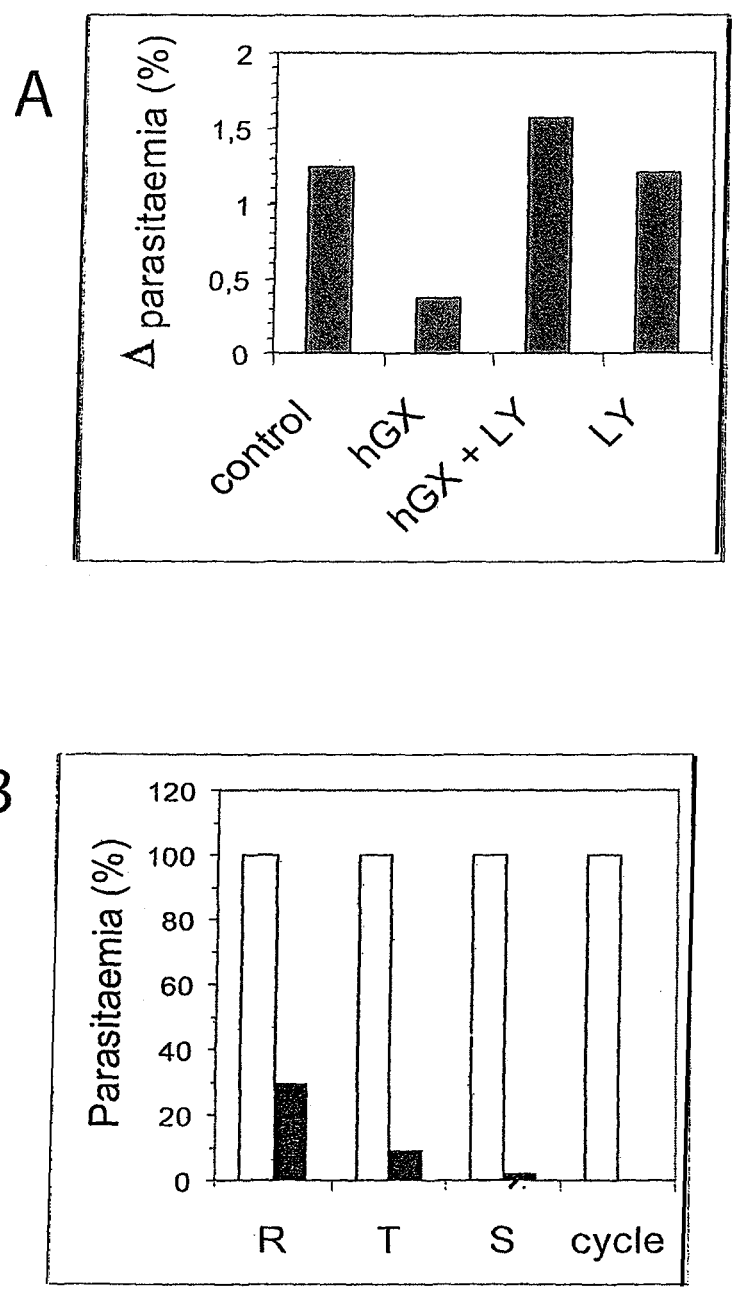
FIG. 4A shows the LY329722 inhibition of the anti-*Plasmodium* effect of GX sPLA$_2$. A schizont-enriched culture was grown for 24 h in the presence of 50 nM recombinant human GX sPLA$_2$ (hGX) or 50 nM human GX sPLA$_2$ plus 37.5 µM LY329722 (hGX+LY); controls were LY329722 alone (LY) and normal culture conditions (control). Parasitaemia (%) at t 0 h and t 24 h were determined from Diff Quick-stained smears. Y axis states increase of parasitaemia (Δ parasitaemia (%)), expressed as parasitaemia at t 24 h-parasitaemia at t 0 h.
FIG. 4B shows the parasite blood stages' sensitivity to human GX sPLA$_2$. A parasite culture was synchronised on a 4 h window. Parasites aged 0-4 h post-invasion (p.i.) (rings, R), 18-22 h p.i. (trophozoites, T), and 34-38 h p.i. (schizonts, S) were incubated for 15 h in culture conditions with (■) or without (□) 100 nM recombinant GX sPLA$_2$. Afterwards cells were washed and let grow in normal culture conditions until re-invasion. GX sPLA$_2$ inhibitory activity on the complete parasite cycle was assessed by incubating 0-4 h p.i. parasites for 48 h with GX sPLA$_2$ (cycle). Parasitaemia in each sample was determined from Diff Quick-stained smears. For each stage, 100% parasitaemia was established from parasite growth in the absence of enzyme.

As it can be seen in FIG. 4B, a 15 h-treatment with recombinant GX sPLA$_2$ is inhibitory to either of the parasite stages Inhibition was largely irreversible. Among the GX sPLA2-treated stages, only rings succeeded into a 25% re-invasion, whereas less than 10% trophozoites and schizonts completed the cycle.

2.3.3) GX sPLA$_2$ Exhibits Membranolytic Activity Against Infected Erythrocytes.

It is well known that alteration of the host erythrocyte membrane occurs during parasite intracellular maturation (Maguire et al., 1991). Those *Plasmodium*-induced changes can modulate the membranolytic activity of sPLA$_2$s (Moll et al., 1990).

The membranolytic activity of the recombinant GX sPLA$_2$ on RBCs infected by either young (ring/young trophozoite) or mature (late trophozoite/schizont) parasites was analysed. Because it was previously shown that bee venom sPLA$_2$ does not interact with the infected erythrocytes (Guillaume et al., 2006), this enzyme was used as a negative control of erythrocyte PL hydrolysis. Parasite cultures were incubated with GX sPLA$_2$ in the absence of serum for 5 h and NEFA production was measured thereafter. Values were normalized according to non-specific release of NEFAs in the absence of enzyme.

Figure 5:
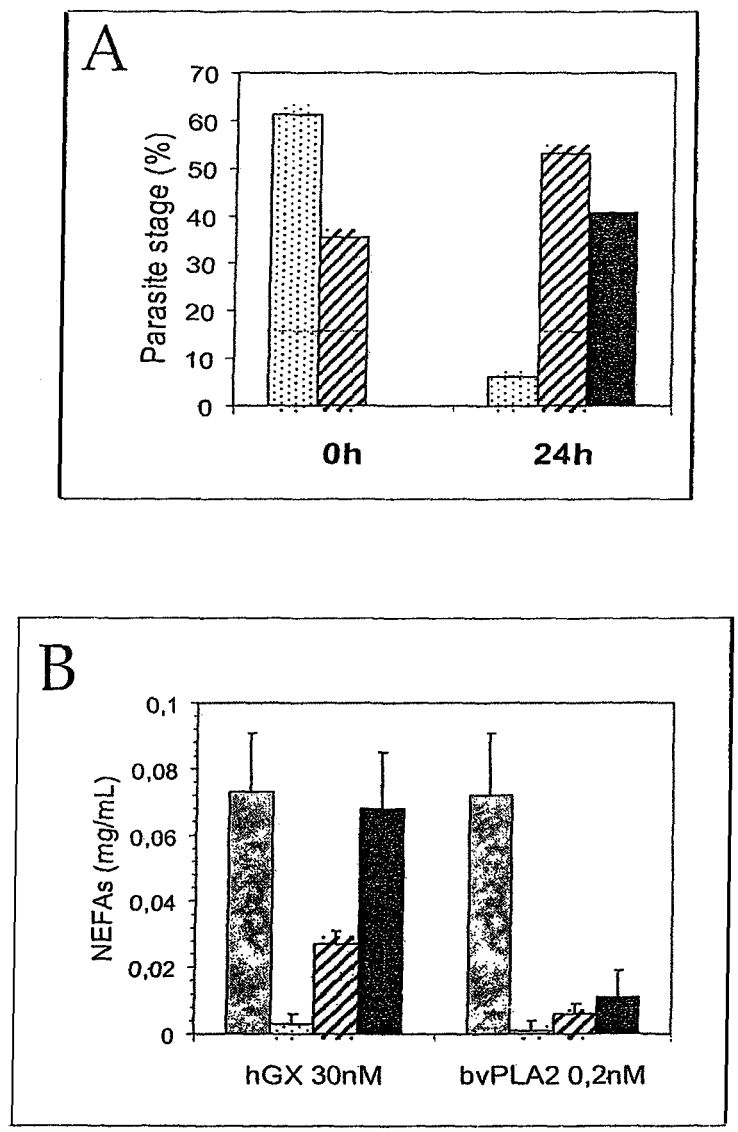
FIG. 5 shows the stage-dependent membranolytic activity of human GX sPLA$_2$. A semi-synchronous culture of *P. falciparum* (2.5% parasitaemia) was analysed for sensitivity to GX sPLA$_2$ at early and late development stages. Parasitaemia and stage distribution were determined from Diff-Quick-stained smears. Early stages were processed at t 0 h and late stages were processed 24 h later (t 24 h). Cultures were washed and cells were re-suspended at 50% haematocrit in RPMI 0.05% BSA, and then distributed into wells of a 96-well microplate in the presence or absence of respectively 30.0 nM of GX sPLA$_2$ and 0.2 nM of bee venom sPLA$_2$. Non-infected erythrocytes and human serum were processed similarly, after all samples had been adjusted for same phosphatidylcholine (PC) content. The microplate was incubated in a candle jar for 5 hours at 37° C. Plasma and cell supernatants were reserved and ghosts were prepared from erythrocytes. NEFAs in each sample were measured in triplicate using the NEFA-C kit (WAKO). A. Stage distribution (% of parasitaemia) at time 0 h and 24 h. Rings: dotted bar; Trophozoites: striped bar. Schizonts: black bar. B. Membranolytic activities of recombinant human GX sPLA$_2$ (hGX) and bee venom sPLA$_2$ (bvPLA$_2$) on plasma (white bar), non-infected erythrocytes (dotted bar), erythrocytes from young parasite-enriched (striped bar) and mature parasite-enriched (black bar) culture. NEFA concentration in cell samples is the sum of NEFAs from paired supernatants and ghosts. Values were normalized by subtracting NEFAs from control without enzyme. Values are the mean±SD of triplicate determination.

Group-X sPLA$_2$ induced the release of NEFAs from the parasite culture with predominance for the schizont stages (FIGS. 5, A and B). Release increased with the parasite maturation. Healthy erythrocytes were left intact. As expected, and contrasting with the human enzyme, the bee venom sPLA$_2$ hydrolysed poorly the erythrocytes, either infected or not.

2.3.4. The Anti-*Plasmodium* Effect of GX sPLA$_2$ is Mediated Mainly by Hydrolysis of Exogenous PLs.

Figure 6:
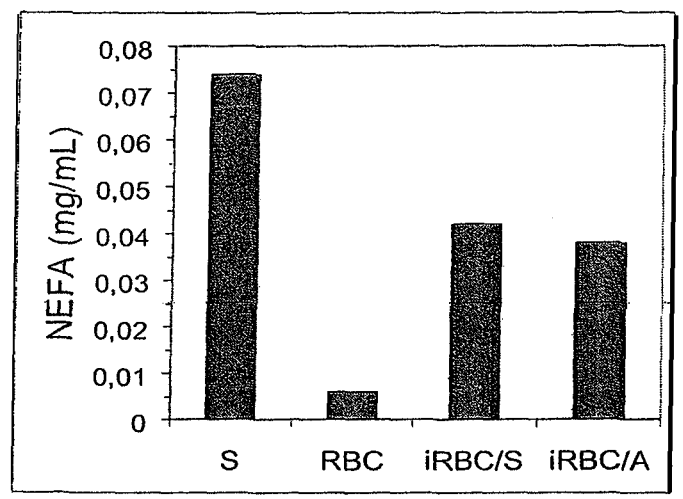
FIG. 6 shows the comparative analysis of the membranolytic activity of human GX sPLA$_2$ on a *P. falciparum* culture grown in serum or in Albumax II®. Parasites were grown in medium containing either 8% human serum (iRBC/S) or 0.5% Albumax II® (iRBC/A). Cultures were semi-synchronized so that they contain mainly mature parasites at the time of the experiment. Both cultures (2.5-3% parasitaemia) were then washed and cells were re-suspended at 50% haematocrit in RPMI 0.05% BSA with or without 50 nM of recombinant GX sPLA$_2$, and incubated for 6 h in culture conditions. Non-infected RBCs (red blood cells) and human serum were processed similarly. Cell supernatants and serum were frozen at −20° C.; erythrocyte ghosts were prepared and frozen. NEFAs in each sample were measured in duplicate upon thawing, using the NEFA-C kit (WAKO). NEFA amount in healthy RBCs (RBC) and in infected cultures (iRBC) is expressed as the sum of NEFAs from paired ghosts and supernatants. Values are the mean of the duplicate measurement, subtracted for values in the absence of enzyme. The experiment was repeated twice and gave similar qualitative results. Results from one experiment are shown.

It was found that GX sPLA$_2$ does not efficiently inhibit *Plasmodium* growth in Albumax II®, regarding its capacity to hydrolyse infected erythrocytes in culture (see Example 2.2.1). To check for possible inhibition of the enzyme by Albumax II®, hydrolysis of *E. coli* membranes was carried out in the presence of Albumax II®. Hydrolysis occurred at the same rate in Albumax II® and in control without Albumax® (not shown), indicating that Albumax II® does not prevent the GX sPLA$_2$ enzymatic activity. It was further examined whether culture in the absence of serum might induce modifications of the erythrocyte membrane that would in turn prevent its hydrolysis by GX sPLA$_2$. The membranolytic activity of GX sPLA$_2$ on a schizont-enriched parasite culture maintained in Albumax II® was analysed. As illustrated in FIG. 6, NEFAs were released at the same rate from the Albumax II®-derived culture and the serum-derived parasite culture, demonstrating that erythrocytes maintained in Albumax II® do not undergo GX sPLA2-inhibiting membrane modifications. Taken together, these results indicate that neither enzyme inhibition nor erythrocyte membrane alteration can explain the Albumax II®-induced drop in toxicity.

2.4) Evaluating the In Vitro Chemosensitizing Properties of PAF on the Anti-*Plasmodium* Activity of GX sPLA2.

The acetylated phospholipid platelet-activating factor (PAF) is a potent pro-inflammatory mediator exhibiting multiple physiological and pathological actions. It is produced by various inflammatory cells and by endothelial cells. The actions of PAF are abolished by hydrolysis of the acetyl residue, a reaction catalysed by PAF acetylhydrolase (PAF-AH), an atypical sPLA$_2$ associated to plasma lipoproteins. It was shown that recombinant GX sPLA$_2$ efficiently hydrolyses PAF (Gora et al; 2006), and it has been proposed that the enzyme be involved in the neutralization of the newly synthesized PAF during LDL oxidation, thereby eliminating its biological activity.

The effects of PAF on the GX sPLA$_2$ anti-*Plasmodium* activity were evaluated. It was first examined whether PAF and/or its degradation products (lyso-PAF and acetate) might affect the *Plasmodium* intra-erythrocytic development. PAF was found to exhibit high IC$_{50}$ value (82.0±1.2 µM) in standard culture conditions. In conditions where the serum PAF-AH was inhibited by Pefabloc, the PAF IC$_{50}$ value did not vary (95.0±2.8 µM), making improbable that PAF or products of PAF generated in normal plasmatic conditions might have any effect on the parasite development.

Figure 7:
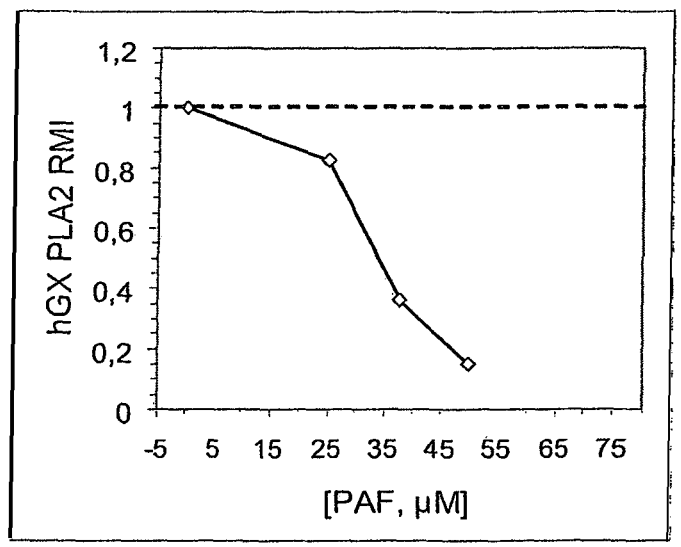
FIG. 7 shows the PAF-induced potentiation of the human GX sPLA$_2$ anti-*P. falciparum* effect. The effects of serial concentrations of PAF (platelet-activating factor) on the susceptibility of the *P. falciparum* FcB1 strain to GX sPLA$_2$ were assessed in vitro. A *P. falciparum* culture (1% parasitaemia, 2% haematocrit) was incubated in a 96-well microplate with decreasing concentrations of the recombinant GX sPLA$_2$ in the presence of a fixed, sub-inhibitory concentration of PAF. The response modification index (RMI) as a function of PAF concentration is represented. RMI is the ratio of the 50% inhibitory concentrations (IC$_{50}$) for GX sPLA$_2$ plus the concentration of PAF, and GX sPLA$_2$ alone. An RMI of 1.0 represents no change in the IC$_{50}$ for GX sPLA$_2$ when combined with PAF. The RMI values<1.0 represent the degree of potentiation or synergism.

The effects of PAF on the anti-*Plasmodium* activity of GX sPLA$_2$ were assessed by GX sPLA$_2$ and PAF interaction studies, in which fixed sub-inhibitory concentrations of PAF were combined with pre-serially diluted GX sPLA$_2$. Concentration-response curves for GX sPLA$_2$ alone and in the presence of PAF were compared. The data were expressed as the response modification index (RMI) (as in Oduola et al., 1998). RMI values were found <1 (FIG. 7), indicating that PAF potentiates the activity of GX sPLA$_2$ against *Plasmodium*.

Example 2

Diagnosis of a *Plasmodium* Infection in a Patient Using a Time-Resolved Fluoroimmunoassay (TR-FIA)

A blood sample from a patient having a non-specific febrile illness is analysed for determining the serum concentration of GIIF, GV and GX sPLA$_2$s by TR-FIA.

The TR-FIA for human GIIF, GV and GX sPLA$_2$s is used as described in Nevalainen et al., 2005. Anti-GIIF, GV and GX sPLA$_2$ IgG isolated from a rabbit are obtained and then labelled. Recombinant human GIIF, GV and GX sPLA$_2$s are used as standards in the TR-FIA.

A serum concentration of the GIIF, GV and/or GX sPLA$_2$s respectively superior to 4, 11 and 2 µg/L is indicative that said patient is infected with *Plasmodium*.

Example 3

Identification and Quantification of Individual sPLA$_2$ Isoforms Including hGIIA, hGIIF, hGV, and hGX in the Plasma of Malaria Patients, sPLA$_2$ Isoform Profiling and Relationship with Parasitaemia and Disease Activity 1) Methods 1.1) sPLA$_2$ Activity Assay sPLA$_2$ enzymatic activity was measured using radiolabeled *E. coli* membranes as substrate, as described in Rouault et al., 2007. Briefly, 2 to 3 µL of plasma were incubated for 30 min in 60 µL of sPLA$_2$ activity buffer (0.1 M Tris pH 8.0, 10 mM CaCl2 and 0.1% BSA) containing 100,000 dpm of [3H]-oleate-radiolabeled *E. coli* membranes. Reactions were stopped by addition of 80 µL of stop buffer (0.1 M EDTA pH 8.0 and 0.5% fatty acid-free BSA). Mixtures were centrifuged at 10,000 g for 5 min, and supernatants containing released [3H]oleate were counted in a Wallac Perkin-Elmer microbeta counter.

1.2) Time-Resolved Fluoroimmunoassays (TR-FIA)

TR-FIA was performed as described in Nevalainen et al., 2005. Briefly, 3 to 5 µL of plasma were diluted in 100 µL of Delfia assay buffer (Perkin Elmer Wallac) and added to GIIA, GIIF, GV and GX sPLA$_2$s IgG-coated microtiter wells previously washed with TR-FIA washing solution (TBS pH 7.8, 0.04% NaN3, 0.02% Tween 20). After incubation at room temperature with constant shaking for 30 minutes, wells were washed 4 times with TR-FIA washing solution, incubated with 100 µL of Eu-labeled human sPLA$_2$ IgG tracer (0.5 µg/mL diluted in Delfia Assay buffer) and washed again 4 times as above. Then 100 µL of Delfia enhancement solution was added to wells, incubated at room temperature for 5 min with shaking and thereafter for 10 min without shaking. Time-resolved fluorescence was measured using a Wallac Envision Perkin Elmer plate reader and optimized optical modules for DELFIA assays.

1.3) Statistical Analysis

Statistical analysis was performed using the GraphPad InStat 3 software.

2) Results

Plasma from patients infected with *Plasmodium falciparum* (n=26, parasitaemia ranging from 0.01% to 4.0%) were analyzed for total sPLA$_2$ activity on *E. coli* membranes and for the presence of individual sPLA$_2$ isoforms including hGIIA, hGIIF, hGV and hGX by TR-FIA. Analysis of 15 plasmas from non infected subjects (control group) was performed in parallel.

Enzymatic activity on *E. coli* membranes was higher in plasma from infected patients than the control group (P=0.0284, using Mann-Whitney test, two-tail P value). However, the level of enzymatic activity was not predictive of parasitaemia or disease activity.

TR-FIA analysis of hGIIA sPLA$_2$ showed a significant elevation of the enzyme mass level in plasma of patients with either low (<0.5%) or high parasitaemia (>0.5%) (P=0.0148 and P=0.0170, respectively, using Mann-Whitney test, two-tail P value). The level of hGIIA sPLA$_2$ mass is therefore not predictive of parasitaemia or disease activity. The level of hGIIA sPLA$_2$ mass measured by TR-FIA was clearly associated with the level of total enzymatic activity (Spearman r=0.6327, P<0.0001).

Independent of these measurements, significant increases of hGV and hGIIF sPLA$_2$s were found in patients with low parasitaemia (P=0.0285 and P=0.0113, respectively, using Mann-Whitney test, two-tail P value), but not in patients with higher parasite levels, as compared to the control group.

No increase in hGX was seen in either group. This is probably because of the small cohort of patients in the present study.

Interestingly, correlation studies between plasma concentrations of the different sPLA$_2$s showed a very strong correlation between the respective levels of hGV and hGIIF sPLA$_2$s (Spearman r=0.5412, P=0.0003) and a slight but significant correlation between levels of hGIIA and hGIIF sPLA$_2$s (Spearman r=0.3889, P=0.0120). No correlation was found between the levels of hGIIA and hGV sPLA$_2$s.

3) Comments

The above results indicate that the specific quantification of individual sPLA$_2$ isoforms in the plasma of malaria patients can provide an independent set of data and/or a combined set of data (sPLA$_2$ isoform profiling) which is associated with the level of parasitaemia. Defining a sPLA$_2$ isoform profile may thus be useful for diagnosis of disease activity, therapeutic follow-up or prediction of patient's outcome.

Three sPLA$_2$ isoforms, namely hGIIA, hGIIF and hGV were found to be significantly increased in patients infected by *P. falciparum*.

No sPLA$_2$s other than hGIIA have been reported to be present in the plasma from normal subjects or septic shock patients (Nevalainen et al., 2005). Although preliminary, the above results indicate that the levels of hGIIF and hGV sPLA$_2$s are specifically increased after infection with the malaria parasite, and thus that these individual sPLA$_2$ isoforms may constitute novel biomarkers of disease activity, especially in patients with low parasitaemia.

The correlation observed between the plasma levels of hGIIF and hGV sPLA$_2$s as well as that observed between hGIIA and hGIIF sPLA$_2$s suggest that the combined measurement of sPLA$_2$ isoforms (sPLA$_2$ isoform profiling) represents a highly specific biomarker of malaria disease activity. For instance, it can be speculated that a specific combined increase of hGIIF and hGV sPLA$_2$s enzymes in plasma of patients with low parasitaemia may contribute to maintain parasitaemia under a deleterious threshold, and may be predictive of patient's outcome. Similarly, the correlation between the levels of hGIIA and hGIIF sPLA$_2$s may be predictive of disease activity.

Consequently, it appears from these results, that the specific assays of sPLA$_2$ isoforms and/or the combined measurement of certain individual sPLA$_2$ isoforms including hGIIA, hGIIF, hGV and hGX sPLA$_2$s is predictive of disease activity and clinical outcome.

REFERENCES

Ait-Oufella, H., et al. 2010. Circulation Abstract 5459, ATVB meeting 2009.
Boilard, E., et al. 2010. *EMBO Mol. Med.* 2: 172-187.
Bostrom, M. A., et al. 2007. *Arterioscler. Thromb. Vasc. Biol.* 27: 600-606.
Chen J., et al. 1994. *J. Biol. Chem.* 269: 2365-2368.
Cupillard L., et al. 1997. *J. Biol. Chem.* 272: 15745-15752.
Deregnaucourt, C., and Schrével, J. 2000. *J. Biol. Chem.* 275: 39973-39980.
Eckey, R., et al., 1997. *Atherosclerosis* 132: 165-176.
Franson, R., et al. 1974. *J. Lipid Res.* 15: 380-388.
Gelb, M. H., et al., 2000. *J. Biol. Chem.* 275: 39823-39826.
Gesquière, L., et al. 2002. *Biochemistry* 41: 4911-4920.
Gilroy, D. W., et al. 2004. *Faseb J.* 18: 489-498.
Gora, S., et al. 2006. *Biochim. Biophys. Acta* 1761: 1093-1099.
Grellier, P., et al. 1990. *C. R. Acad. Sci. III.* 311: 361-367.
Guillaume, C. et al. 2004. *Toxicon* 43: 311-318.
Guillaume, C., et al. 2006. *J. Lipid Res.* 47: 1493-1506.
Havel, R. J., et al. 1955. *J. Clin. Invest.* 34: 1345-1353.
Ishimoto, Y., et al. 2003. *BBA.* 1642: 129-138.
Ishizaki J., et al. 1999. *J. Biol. Chem.* 274: 24973-24979.
Jonsson-Rylander, A. C., et al. 2008. *Curr. Atheroscler. Rep.* 10: 252-259.
Kudo, I., and Murakami, M. 2002. *Prostaglandins Other Lipid Mediators.* 68-69: 3-58.
Koduri, R. S., et al. 2002. *J. Biol. Chem.* 277: 5849-5857.
Kramer, R. M., et al. 1989. *J. Biol. Chem.* 264: 5768-5775.
Lambeau, G., and Gelb, M. H. 2008. *Annu. Rev. Biochem.* 77: 495-520.
Maguire, P. A., et al. 1991. *Parasitology.* 102: 179-186.
Moll, G. E., et al. 1990. *Biochim. Biophys. Acta* 1024: 189-192.
Murakami, M., et al. 2010. *Biochimie.* 92: 561-582.
Nakanishi, M., and Rosenberg, D. W. 2006. *Biochim. Biophys. Acta* 1761: 1335-1343.

Nevalainen, T. J., et al., 2005. *Biochim. Biophys. Acta* 1733: 210-223.
Nevalainen, T. J., et al. 2008. *Biochim. Biophys. Acta* 1781: 1-9.
Oduola, A. M., et al. 1998. *Am. J. Trop. Med. Hyg.* 58: 625-629.
Oufella, H., et al. 2010. Circulation Abstract 5459, ATVB meeting 2009.
Pruzanski, W., et al. 1998. *J. Lipid Res.* 39: 2150-2160.
Pruzanski, W., et al. 2005. *Biochim. Biophys. Acta.* 1736: 38-50.
Rosengren, B., et al. 2006. *Biochim. Biophys. Acta* 1761: 1301-1308.
Rouault, M., et al. 2003. *Biochemistry* 42: 11494-11503.
Rouault, M., et al. 2007. *Biochemistry* 46: 1647-1662.
Rosengren, B. A., et al. 2006. *Biochim. Biophys. Acta* 1761: 1301-1308.
Sato, H., et al., 2008. J. Biol. Chem. 283:33483-33497.
Schaloske, R. H., and E. A. Dennis. 2006. *BBA*. 1761: 1246-1259.
Seilhamer, J. J., et al. 1986. *DNA* 5: 519-527.
Seilhamer, J. J., et al. 1989. *J. Biol. Chem.* 264: 5335-5338.
Sibmooh, N., et al., 2004. *Lipids Health Dis.* 3: 15.
Singer, A. G., et al. 2002. *J. Biol. Chem.* 277: 48535-48549.
Six, D. A., and Dennis, E. A. 2000. *Biochim. Biophys. Acta* 1488: 1-19.
Smart, B. P., et al. 2006. *J. Med. Chem.* 49: 2858-2860.
Sun, G. Y., et al. 2007. *J. Neurochem.* 103: 1-16.
Suzuki, N., et al. 2000. *J. Biol Chem.* 275: 5785-5793.
Talvinen, K. A., and Nevalainen, T. J. 2002. *Comp. Biochem. Physiol. B. Biochem. Mol. Biol.* 132: 571-578.
Trager, W., and Jensen, J. B. 1976. *Science.* 193: 673-677.
Triggiani, M., et al. 2005. *J. Allergy Clin. Immunol.* 116: 1000-1006.
Vadas, P., et al. 1992. *Infect. Immun.* 60: 3928-3931.
Vadas, P., et al. 1993. *Am. J. Trop. Med. Hyg.* 49: 455-459.
Valentin E., et al. 1999. *J. Biol. Chem.* 274: 31195-31202.
Valentin E., et al. 2000a. *J. Biol. Chem.* 275: 7492-7496.
Valentin, E., et al. 2000b. *Biochem. Bioph. Res. Co.* 279: 223-228.
Valentin, E., et al. 2000c. *Biochim. Biophys. Acta.* 1488: 59-70.
Van der Heyde, H. C., et al. 2006. *TRENDS in Parasitol.* 22: 503-508.
Venable, M. E., et al. 1993. *J. Lipid Res.* 34: 691-702.
Verheij, H. M., et al. 1981. *Rev. Physiol. Biochem. Pharmacol.* 91: 91-203.
Von Allmen, C. E., et al. 2009. *Proc. Natl. Acad. Sci. USA.* 106: 11673-11678.
Warhurst, D. C., and Williams, J. E. 1996. *J. Clin. Pathol.* 49: 533-538.
Webb, N. R., et al. 2003. *Arterioscler. Thromb. Vasc. Biol.* 23: 263-268.

The invention claimed is:

1. An in vitro method of diagnosis of a *Plasmodium* infection in a subject, comprising the following steps:
   a) measuring a serum concentration of at least one secreted phospholipase A2 (sPLA2) selected from the group consisting of GIIF, GV and GX sPLA2s, in a blood sample from said subject,
   b) comparing the serum concentration of GIIF, GV and/or GX sPLA2s obtained in step a) with a reference serum concentration of GIIF, GV and/or GX sPLA2s in subjects not infected with *Plasmodium* respectively, wherein an increased serum concentration of GIIF, GV and/or GX sPLA2s in said blood sample from said subject compared to the reference serum concentration of GIIF, GV and/or GX sPLA2s in subjects not infected with *Plasmodium* is indicative that said subject is infected with *Plasmodium*.

2. The method according to claim 1, wherein in addition to the measurement of the serum concentration of GIIF, GV and/or GX sPLA2s, a serum concentration of GIIA sPLA2 is also measured, wherein an increased serum concentration of GIIF, GV and/or GX sPLA2s, and GIIA sPLA2 in said blood sample from said subject compared to the reference serum concentration of GIIF, GV and/or GX sPLA2s, and GIIA sPLA2 in subjects not infected with *Plasmodium* is indicative that said subject is infected with *Plasmodium*.

3. The method according to claim 2, wherein said subject is a human, and wherein said increased serum concentration of GIIF, GV and/or GX sPLA2s in said blood sample, is respectively greater than 4, 11 and 2 µg/L, and said increased serum concentration of GIIA in said blood sample is greater than 10 µg/L, measured with an appropriate immunoassay.

4. The method according to claim 2, wherein the measurement of the serum concentration of the GIIA, GIIF, GV and/or GX sPLA2s is carried out in vitro by measuring the catalytic activity of said sPLA2s or by immunoassay.

5. The method according to claim 2, wherein the serum concentration of GIIF and/or GV sPLA2s, and in addition GIIA sPLA2, is measured, and wherein an increased serum concentration of GIIF and/or GV sPLA2s, and GIIA sPLA2, in said blood sample from said subject compared respectively to the reference serum concentration of GIIF and/or GV and GIIA sPLA2s in subjects not infected with *Plasmodium*, is further indicative that said subject is infected with *Plasmodium* with low parasitaemia.

6. The method according to claim 2, wherein said increased serum concentration of GIIF and/or GV sPLA2s, and GIIA sPLA2, in said blood sample from said subject is further indicative that said subject is in remission.

7. The method according to claim 1, wherein the measurement of the serum concentration of the GIIF, GV and/or GX sPLA2s is carried out in vitro by measuring the catalytic activity of said sPLA2s or by immunoassay.

8. The method according to claim 1, wherein said subject is a human, and wherein said increased serum concentration of GIIF, GV and/or GX sPLA2s in said blood sample, is respectively greater than 4, 11 and 2 µg/L measured with an appropriate immunoassay.

9. The method according to claim 8, wherein said increased serum concentration of GIIF, GV and/or GX sPLA2s in said blood sample, is respectively greater than 8, 20 and 4 g/L measured with an appropriate immunoassay.

10. The method according to claim 1, wherein the *Plasmodium* infection is a *P. falciparum* infection.

11. The method according to claim 1, wherein the serum concentration of GIIF and OX sPLA2s, or GIIF, GV and GX sPLA2s is measured.

12. The method according to claim 1, wherein the serum concentration of GIIF and/or GV sPLA2s is measured, and wherein an increased serum concentration of GIIF and/or GV sPLA2s in said blood sample from said subject compared respectively to the reference serum concentration of GIIF and/or GV sPLA2s in subjects not infected with *Plasmodium*, is further indicative that said subject is infected with *Plasmodium* with low parasitaemia.

13. The method according to claim 1, wherein said increased serum concentration of GIIF and/or GV sPLA2s in said blood sample from said subject is further indicative that said subject is in remission.

* * * * *

UNITED STATES PATENT AND TRADEMARK OFFICE
CERTIFICATE OF CORRECTION

PATENT NO. : 8,709,741 B2  Page 1 of 1
APPLICATION NO. : 13/513465
DATED : April 29, 2014
INVENTOR(S) : Deregnaucourt et al.

It is certified that error appears in the above-identified patent and that said Letters Patent is hereby corrected as shown below:

In the claims:

Column 22,
Line 47, "4 g/L" should read --4 µg/L--;
Line 52, "OX" should read --GX--.

Signed and Sealed this
Twenty-ninth Day of July, 2014

Michelle K. Lee
*Deputy Director of the United States Patent and Trademark Office*